United States Patent [19] [11] 4,021,465
Fozzard et al. [45] May 3, 1977

[54] UNSATURATED DINITRILE PREPARATION

[75] Inventors: George B. Fozzard; John R. Norell, both of Bartlesville, Okla.

[73] Assignee: Phillips Petroleum Company, Bartlesville, Okla.

[22] Filed: Jan. 13, 1976

[21] Appl. No.: 648,709

[52] U.S. Cl. .................. 260/465.8 R; 260/464; 260/465 H

[51] Int. Cl.$^2$ ..................................... C07C 120/00

[58] Field of Search ............... 260/465.8 R, 465 H, 260/464

[56] References Cited

UNITED STATES PATENTS

| | | | |
|---|---|---|---|
| 2,641,607 | 6/1953 | Albisetti, Jr. et al. | 260/465.3 |
| 3,247,237 | 4/1966 | Hagemeyer, Jr. | 260/465.9 |
| 3,840,583 | 10/1974 | Turk et al. | 260/465.8 R |

OTHER PUBLICATIONS

Albisetti, et al.; J.A.C.S., 78, (1956), pp. 2637–2641.
Hoffmann, Angewandti Chemie, vol. 8, (1969), pp. 556–577.

Primary Examiner—Joseph Paul Brust

[57] ABSTRACT

In processes of preparing unsaturated dinitriles from olefins, unsaturated mononitriles, and a monoadduct reaction product of an olefin and an unsaturated mononitrile in which undesirable internally unsaturated monoadduct is formed, the improvement of inhibiting the formation of internally unsaturated monoadduct by decomposing at least a portion of the recycle stream of monoadduct to form olefin and unsaturated mononitrile, and passing the thus-formed olefin and unsaturated mononitrile to the reaction.

10 Claims, No Drawings

UNSATURATED DINITRILE PREPARATION

This invention relates to an improved process for the preparation of unsaturated dinitriles. In another aspect, this invention relates to an improved process for producing $C_{10}$ dinitriles from acrylonitrile and isobutylene whereby the production and buildup of 5-methyl-4-hexenenitrile is minimized. In accordance with a further aspect, this invention relates to an improved process for producing unsaturated $C_{10}$ dinitriles from acrylonitrile, isobutylene, and an unsaturated $C_7$ nitrile (monoadduct) by subjecting at least a portion of the recycle stream of monoadduct to decomposition conditions which produces isobutylene and acrylonitrile, which materials are passed to the initial reaction for monoadduct formation. In still another aspect, this invention relates to a method for producing mixed isomeric $C_{10}$ dinitriles useful for producing fiber grade polyamides.

U.S. Pat. No. 3,840,583 discloses a process for the production of unsaturated dinitriles from the reaction of two moles of acrylonitrile with one mole of isobutylene. Said dinitriles are formed in a stepwise reaction in which an intermediate unsaturated mononitrile is first formed from one mole of acrylonitrile and one mole of isobutylene. For convenience in the discussion hereinafter, the unsaturated mononitrile will be referred to as monoadduct and the unsaturated dinitrile as diadduct. It is also known that the hydrogenation of said diadduct produces a saturated diamine mixture which is predominantly 5-methyl-1,9-nonanediamine (MND) and which can be employed in the preparation of various condensation type polymers. In particular, it has been found that MND with terephthalic acid produces a polyamide which has a very desirable set of properties for use as a fiber, e.g., U.S. Pat. No. 3,839,295.

In the course of the development of fiber grade polyamides from the above-mentioned saturated diamines (MND) and dibasic acids, it was discovered that certain lots of diamine (MND) produced from the diadduct provided polymer properties having reduced values in tenacity and the like. It was discovered by careful analysis of the various lots of MND that certain highly branched isomeric diamines appeared to be responsible for the undesirable properties in the final polyamide polymer. In particular, the compound 4-isopropyl-1,7-heptanediamine was identified as one isomer which produced the undesirable polyamide properties. It was found that the occurrence of this isomer could be traced back to an isomerization reaction in the monoadduct. Specifically, the principal isomeric compound in the monoadduct is 5-methyl-5-hexenenitrile which can isomerize to 5-methyl-4-hexenenitrile. It is also possible that the latter compound may form directly from isobutylene and acrylonitrile in a small amount. Whether or not the compound is formed directly or by isomerization of the principal monoadduct product, it is known that the 5-methyl-4-hexenenitrile on reaction with acrylonitrile produces 4-isopropenyl-heptane-dinitrile which on hydrogenation gives rise to the undesirable isomer 4-isopropyl-1,7-heptanediamine. It is believed that for acceptable fiber properties in the polyamide produced from MND and terephthalic acid that the amount of said undesirable isomer should be less than about 0.5 weight percent of the diamine employed.

The problem caused by the undesirable isomer precursor, 5-methyl-4-hexenenitrile, is further magnified by the process employed to produce the diadduct. In said preferred process, the monoadduct serves as the reaction diluent, and in a single reaction zone acrylonitrile and isobutylene are introduced in the presence of preformed monoadduct to produce the diadduct with suitable adjustments of the molar ratios of acrylonitrile to isobutylene so that there is essentially no net gain nor loss of the monoadduct in the reaction mixture. The effluent from the above-described reaction zone is simply fractionated to provide monoadduct which is recycled to the reaction zone and diadduct which is then taken to the hydrogenation step for production of the diamine. It has been discovered that the undesirable isomer precursor, 5-methyl-4-hexenenitrile, reacts with acrylonitrile three to four times as slow as the normal monoadduct 5-methyl-5-hexenenitrile and thus on continued recycle of the monoadduct to the reaction zone where diadduct is being formed will eventually provide for a buildup of a significant amount of the precursor of the undesired diamine isomer. This, of course, explains why the presence of the 4-isopropyl-1,7-heptanediamine was not observed until after the process had been operating for some time and the level of monoadduct precursor for this undesired isomer had built up to a substantial or significant degree.

Since the undesirable isomer monoadduct precursor reacts significantly slower than the normal monoadduct isomer, one possible solution would be to simply draw off a portion of the monoadduct recycle stream and purify it by fractional distillation to effectively remove the 5-methyl-4-hexenenitrile isomer. However, this has proved to be essentially impractical because of the very close boiling points of the two isomeric monoadducts.

Another possible solution would be to simply withdraw a portion of the recycle monoadduct stream and discard the same. However, this would obviously be an expensive solution and would effectively consume valuable chemicals without producing the desired diadduct from the process. Furthermore, a suitable means of disposal would also be required that would satisfy environmental considerations in the method utilized for said disposal. This also could add to the economic penalty for this solution to the problem.

Neither of the two possible solutions to the above-described problem appear to be desirable, and thus the instant invention is seen as a means of solving the above-described problem in a simple and yet economically valuable manner.

Accordingly, an object of this invention is to minimize the formation of undesirable internally unsaturated monoadduct in processes of preparing unsaturated dinitriles.

A further object of this invention is to provide a process for preparing isomeric $C_{10}$ unsaturated dinitriles in which the formation of $C_{10}$ unsaturated dinitriles unsuitable for the production of fiber grade polyamides is minimized.

Other objects, aspects, and the several advantages of the invention will be apparent to those skilled in the art upon a study of this disclosure and the appended claims.

According to the invention, an improved process is provided for the preparation of unsaturated dinitriles from an olefin, an unsaturated mononitrile, and a monoadduct reaction product of an olefin and an unsaturated mononitrile whereby the production of and buildup of undesirable internally unsaturated monoadduct is minimized by subjecting at least a portion of the recycle stream of monoadduct to conditions of temperature and for a period of time sufficient to decompose the monoadduct into olefin and unsaturated mononitrile which materials can be passed to the initial reaction. It has been found that the treatment of the recycle stream of monoadduct as set forth herein prevents the buildup of an undesirable slower reacting monoadduct isomer.

According to a specific embodiment of the instant invention, the above-described problem of preventing a significant accumulation of 5-methyl-4-hexenenitrile in the monoadduct which in turn gives rise to 4-isopropenylheptanedinitrile and ultimately to 4-isopropyl-1,7-heptanediamine is achieved by withdrawing a portion of the recycle monoadduct stream and thermally cracking or pyrolyzing said bleed stream to products comprising acrylonitrile and isobutylene. Since acrylonitrile and isobutylene are reactants in the process for making monoadduct and subsequently diadduct, they can be recycled to the reaction zone from the cracking zone after separation from other materials which may be present. It is readily apparent that this method of treating the bleed stream from the monoadduct recycle stream provides a very desirable solution to the problem in that acrylonitrile and isobutylene are regenerated and that 5-methyl-4-hexenenitrile can be maintained at an acceptably low level in the monoadduct stream.

The amount of monoadduct recycle stream which is bled off to the cracking zone is broadly within the range of from about 5 to about 50 and preferably from 10 to 20 weight percent. The amount of undesired isomer formed in the reaction zone in a given time period will generally depend on the reaction conditions and thus the level of said undesired isomer in the monoadduct recycle stream will also generally depend on the reaction conditions. It is, of course, possible for analysis to be carried out from time to time on the monoadduct recycle stream in order to provide a check on the level of the undesired isomeric compound. Such analysis results then could be employed to change the amount of recycle stream which is bled off to the cracking zone. Generally speaking, the lower the amount of undesired monoadduct isomer required in the monoadduct stream, the larger the amount of recycle stream which may be taken off to the cracking zone.

As indicated above, the portion of the recycle stream of monoadduct treated in accordance with the invention is subjected to conditions including an elevated temperature and a period of time and other process variables sufficient to cause decomposition of the monoadduct to form olefin and unsaturated mononitrile. The decomposition can be carried out under pyrolysis or cracking conditions which can vary appreciably, dependent upon the temperature employed and the length of time the monoadduct is subjected to the elevated temperature.

In general, the monoadduct cracking zone is operated broadly within a temperature range of from about 480° C to about 650° C and preferably from 525° C to 575° C.

The residence time for the monoadduct bleed stream in the cracking zone can be broadly from 0.1 second up to 10 minutes, but preferably from 1 to 20 seconds. Since the cracking step is predominantly the conversion of one molecule of diadduct to two molecules of product, it is expected that the reaction would be favored by the use of reduced pressure in the cracking zone. However, the cracking step can be carried out at a pressure of from about 0.14 to about 690 kPa and preferably from 34 to 205 kPa (kiloPascals).

It is optional though presently preferred that the bleed stream from the monoadduct recycle stream be admixed with an essentially inert gaseous diluent before entering the cracking zone. Suitable diluents which can be employed in this embodiment include helium, argon, nitrogen, carbon dioxide, and steam. Broadly, the gaseous diluent can be utilized in a molar ratio of diluent/monoadduct of from 0.1/1 to 50/1.

The cracking reaction under the conditions described above can be carried out in any convenient reactor configuration such as, for example, a heated pipe or a pipe filled with essentially inert material such as glass beads, carbon rings, stainless steel beads, and the like.

As described above, the cracking of the bleed stream from the monoadduct recycle stream provides an effluent from the cracking zone which comprises acrylonitrile and isobutylene. The selectivity to acrylonitrile and isobutylene can be as high as 88 percent at a 90 percent conversion of monoadduct bleed stream. The effluent from the cracking zone may also contain unreacted monoadduct as well as smaller amounts of heavy material, usually 6 percent or less. The products from the cracking zone can be easily and conveniently separated by distillation and the acrylonitrile and isobutylene returned directly to the reaction zone for the preparation of monoadduct and diadduct. Unreacted monoadduct can, of course, be recycled to said same reaction zone or to the cracking zone.

The reaction conditions, ratios of reactants, etc., for the preparation of unsaturated dinitriles from olefins, unsaturated mononitriles, and a monoadduct reaction product can vary appreciably and are generally set forth in U.S. Pat. No. 3,840,583, which is incorporated herein by reference. Any suitable reaction conditions for either a batch process or a continuous process can be employed. As seen in column 3, lines 49–50 of U.S. Pat. No. 3,840,583 the olefin hydrocarbon contains from 3 to 12 carbon atoms with 1 to 2 ethylenically unsaturated, nonconjugated double bonds and as seen in column 3, lines 63 to 72 the mononitrile has from 3 to 10 carbon atoms per molecule and is represented by the formula RCH=CR — CN, wherein each R is independently selected from alkyl, cycloalkyl, and aryl hydrocarbyl radicals and combinations thereof and hydrogen.

EXAMPLES

The monoadduct cracking runs were carried out according to the instant invention in the following manner:

The feed is charged to a Fischer-Porter pressure tube and pressurized with nitrogen, from which it is passed through a Rotometer and into a tee, at which point nitrogen is admixed therewith also through a Rotometer. From the tee the feed/nitrogen mixture is passed to the cracking reactor. From the cracking reactor the effluent passes through a sample port from which samples are withdrawn for analysis and to a wet ice trap followed by a dry ice trap which recovers the condensible products from the cracking zone.

In the runs of Example I, the cracking reactor itself was a heavy walled nickel tube of 19 millimeters in internal diameter by 660 millimeters in length. In the runs of Examples II and III, the reactor was a stainless steel tube of 19 millimeters internal diameter by 330 millimeters in length filled with 85 milliliters of glass beads of 4 millimeter diameter.

EXAMPLE I

In the apparatus described above, a series of runs were carried out in which a monoadduct stream of approximately 98 percent by weight of 5-methyl-5-hexenenitrile and 2 percent by weight of 5-methyl-4-hexenenitrile was thermally cracked to produce an effluent comprising isobutylene and acrylonitrile and unreacted monoadduct. Samples of the effluent for GLC analysis were taken downstream of the cracking zone and prior to the first ice trap. The results obtained in these runs, as well as the conditions employed, are shown below in Table I.

TABLE I

| Run No. | Temp., °C | Flow Rates[d] MA[a], cc/min | N$_2$, cc/min | Residence Time, Seconds | GLC Area Percent[c] Iso-butylene | ACN[b] | MA[a] |
|---|---|---|---|---|---|---|---|
| 1 | 490 | 20 | 10 | 26.4 | 1.5 | 1.7 | 98 |
| 2 | 550 | 60 | 21 | 9 | 18 | 40 | 25 |
| 3 | 575 | 60 | 21 | 9 | 22 | 65 | — |
| 4 | 579 | 60 | 21 | 9 | 19 | 48 | 3.3 |

[a] MA = monoadduct.
[b] ACN = acrylonitrile.
[c] Other products in the GLC samples for Runs 2 – 4 were not identified.
[d] Flow rates are for gaseous state. Molar ratios of N$_2$/MA are approximately the same as the respective flow rate ratios.

EXAMPLE II

Other runs were carried out employing the same monoadduct composition as used in the runs of Example I in a different reactor which is described above. The results from these runs are presented in Table II below.

TABLE II

| Run No. | Temp., °C | Flow Rates[a] MA, cc/min | N$_2$, cc/min | Residence Time, Seconds | GLC Area %[b] Iso-butylene | ACN | MA |
|---|---|---|---|---|---|---|---|
| 5 | 562 | 60 | 20 | 9 | 36 | 34 | 10 |
| 6 | 558 | 60 | 60 | 6 | 35 | 38 | 11 |
| 7 | 568 | 120 | 60 | 4.2 | 33 | 29 | 25 |

[a] See Footnote (d) of Table I.
[b] Other products in the GLC samples were not identified.

EXAMPLE III

Other runs were carried out using the same reactor as employed in the runs of Example II, but in these runs the monoadduct feed to the cracking zone was composed of approximately equal parts by weight of 5-methyl-5-hexenenitrile and 5-methyl-4-hexenenitrile. The results of these runs are shown below in Table III along with the reaction conditions employed.

TABLE III

| Run No. | Temp., °C | Flow Rates[a] MA, cc/min | N$_2$, cc/min | Residence Time, Seconds | GLC Area %[b] Iso-butylene | ACN | MA |
|---|---|---|---|---|---|---|---|
| 8 | 640 | 48 | 26 | 10.2 | 46 | 12 | — |
| 9 | 615 | 32 | 26 | 13.2 | 46 | 13 | 4 |
| 10 | 585 | 26 | 26 | 13.8 | 34 | 12 | 14 |
| 11 | 560 | 26 | 26 | 13.8 | 35 | 12 | 21 |
| 12 | 530 | 26 | 26 | 13.8 | 12 | 4 | 62 |

[a] See footnote (d) of Table I.
[b] See footnote (b) of Table II.

The results shown in Tables I, II, and III demonstrate that the monoadduct over a wide range of composition for the isomeric unsaturated mononitriles can be thermally cracked to produce reaction mixtures comprising isobutylene and acrylonitrile.

We claim:

1. In a process for preparing unsaturated dinitriles comprising reacting an olefin hydrocarbon having from 3 to 12 carbon atoms with 1 to 2 ethylenically unsaturated, non-conjugated double bonds, an unsaturated mononitrile having from 3 to 10 carbon atoms per molecule and being represented by the formula RCH=CR—CN wherein each R is independently selected from alkyl, cycloalkyl, and aryl hydrocarbyl radicals and combinations thereof and hydrogen, and a monoadduct reaction product of an olefin and an unsaturated mononitrile, as defined above, separating the effluent from said reacting into a product stream comprising unsaturated dinitrile reaction product and a stream comprising monoadduct reaction product for recycle to said reacting, the improvement for minimizing the buildup of internally unsaturated monoadduct recycled to said reacting which comprises subjecting at least a portion of the monoadduct reaction product recycle stream to pyrolysis conditions including an elevated temperature and a period of time sufficient to cause decomposition of said monoadduct and form olefin and unsaturated mononitrile, as defined above, and passing olefin and unsaturated mononitrile thus formed to said reacting.

2. A process according to claim 1 wherein the amount of said monoadduct recycle stream which is subjected to decomposition ranges from about 5 to about 50 weight percent of said recycle stream, and said portion is subjected to pyrolysis at an elevated temperature in the range of about 480° to about 650° C.

3. A process according to claim 1 wherein said portion of said monoadduct reaction product is subjected to pyrolysis at an elevated temperature in the range of about 480° C to about 650° C, the effluent from said pyrolysis is separated into a first stream comprising olefin and unsaturated mononitrile and a second stream comprising other materials including unconverted monoadduct, and said first stream is passed to said reacting as at least a portion of the feed reactants.

4. A process according to claim 1 wherein said olefin is isobutylene, said unsaturated mononitrile is acrylonitrile, and said internally unsaturated monoadduct is 5-methyl-4-hexenenitrile, and the amount of monoadduct subjected to decomposition is in the range of about 10 to about 20 weight percent of the total recycle.

5. A process according to claim 1 wherein the monoadduct is subjected to pyrolysis at a temperature in the range of about 480° C to about 650° C and an inert gaseous diluent is introduced into said monoadduct prior to pyrolysis.

6. A process according to claim 5 wherein said inert gaseous diluent is selected from helium, argon, nitrogen, carbon dioxide, and steam and further wherein the amount of gaseous diluent utilized is in a molar ratio of diluent to monoadduct of from 0.1/1 to 50/1.

7. In the production of an unsaturated $C_{10}$ dinitrile (diadduct) from acrylonitrile, isobutylene, and an unsaturated $C_7$ nitrile (monoadduct), the method of inhibiting the formation of 5-methyl-4-hexenenitrile during the preparation of isomeric $C_{10}$ unsaturated dinitrile which comprises subjecting a minor portion of the recycle stream of monoadduct to pyrolysis conditions including an elevated temperature and a period of time sufficient to cause decomposition and said monoadduct and form isobutylene and acrylonitrile, thereby minimizing the production and buildup of undesirable internally unsaturated monoadduct.

8. A process according to claim 7 wherein said minor portion ranges from about 5 to about 50 weight percent and is subjected to an elevated temperature in the range of about 480° C to about 650° C and said isobutylene and acrylonitrile formed are passed to the reaction for formation of said isomeric $C_{10}$ unsaturated dinitrile.

9. A process according to claim 7 wherein the effluent from said portion subjected to pyrolysis is separated into a stream comprising acrylonitrile and isobutylene which is passed to the reaction for formation of isomeric $C_{10}$ unsaturated dinitrile, and further wherein an inert gas is added to said portion prior to being subjected to said elevated temperature.

10. A process according to claim 7 wherein said portion is subjected to an elevated temperature in the range of about 525° C to about 575° C, the amount of monoadduct recycle stream subjected to said elevated temperature ranges from about 10 to about 20 weight percent of the total recycle, and further wherein an inert gas is introduced into said portion prior to being subjected to said elevated temperature and the isobutylene and acrylonitrile formed during the heating of said monoadduct are passed to the reaction for the formation of isomeric $C_{10}$ unsaturated dinitrile.

* * * * *